(12) United States Patent
Tzeng et al.

(10) Patent No.: US 9,624,467 B2
(45) Date of Patent: Apr. 18, 2017

(54) **BIOCONTROL FORMULATION CONTAINING *STREPTOMYCES* SPP., METHOD FOR PREPARING THE FORMULATION AND RELEVANT USE**

(71) Applicants: Dean Der-Syh Tzeng, Taichung (TW); Win-De Huang, Taichung (TW); Hsin-Chih Ko, Taichung (TW)

(72) Inventors: Dean Der-Syh Tzeng, Taichung (TW); Win-De Huang, Taichung (TW); Hsin-Chih Ko, Taichung (TW)

(73) Assignee: NATIONAL CHUNG HSING UNIVERSITY, Taichung (TW)

( * ) Notice: Subject to any disclaimer, the term of this patent is extended or adjusted under 35 U.S.C. 154(b) by 115 days.

(21) Appl. No.: 14/068,954

(22) Filed: Oct. 31, 2013

(65) Prior Publication Data
US 2014/0057336 A1      Feb. 27, 2014

Related U.S. Application Data

(63) Continuation of application No. 11/708,524, filed on Feb. 20, 2007, now abandoned, which is a continuation-in-part of application No. 11/125,571, filed on May 10, 2005, now abandoned.

(51) Int. Cl.
| | | |
|---|---|---|
| *C12N 3/00* | (2006.01) | |
| *A01N 63/00* | (2006.01) | |
| *A61K 35/742* | (2015.01) | |
| *C12N 1/20* | (2006.01) | |

(52) U.S. Cl.
CPC .............. *C12N 3/00* (2013.01); *A01N 63/00* (2013.01); *A61K 35/742* (2013.01); *C12N 1/20* (2013.01)

(58) Field of Classification Search
CPC . C12N 3/00; C12N 1/20; A01N 63/00; A01N 35/742
See application file for complete search history.

(56) References Cited

U.S. PATENT DOCUMENTS

| 4,132,778 A | 1/1979 | Hamill et al. |
| 5,686,273 A | 11/1997 | Eisenschink et al. |
| 2002/0000540 A1 | 1/2002 | Smither-Kopperl |

OTHER PUBLICATIONS

W-B Chae et al., Ehancing the sporulation of *Streptomyces kasugaensis* by culture optimization, Korean J. Chem. Eng., vol. 26, No. 2, Mar. 2009, pp. 438-443.

*Primary Examiner* — Taeyoon Kim
(74) *Attorney, Agent, or Firm* — Cantor Colburn LLP

(57) ABSTRACT

The present invention is a method for preparing a biocontrol formulation by the following steps. A *Streptomyces* bacterium is selected simultaneously with superior sporulation ability, chitinase activity and antagonistic effectiveness against plant fungal pathogens by culturing with fungal pathogens, wherein the selected *Streptomyces* bacterium is cultured on a chitin-limited plate to assess the ability of sporulation and chitinase activity, and the *Streptomyces* bacterium with superior sporulation ability is the strain with producing powder-like and maturity form spore chains. Spores from the selected bacterium is collected. The obtained spores are taken as a seed inoculum. Then the seed inoculum is cultured to directly yield a broth medium containing at least $10^9$ viable spores/ml which the spores contained in the broth medium are well suspended. The biocontrol formulation is obtained. The present invention further provided a biocontrol formulation containing a high concentration of *Streptomyces* spp. spores.

9 Claims, 9 Drawing Sheets

BIOCONTROL FORMULATION CONTAINING *STREPTOMYCES* SPP., METHOD FOR PREPARING THE FORMULATION AND RELEVANT USE

The present application is a continuation of U.S. Non-Provisional patent application Ser. No. 11/708,524, filed on Feb. 20, 2007. The 11/708,524 application is a continuation in part (CIP) application of U.S. Non-Provisional patent application Ser. No. 11/125,571 filed on May 10, 2005. Priority to each of the above applications is claimed herein, and each of the above applications is incorporated herein by reference.

BACKGROUND OF THE INVENTION

1. Field of the Invention

The present invention relates to a biocontrol formulation, and relates in particular to a biocontrol formulation containing high concentration of viable *Streptomyces* spp. spores. The present invention also relates to a method for preparing the above biocontrol formulation and a method using the formulation.

2. Description of Related Art

The use of agrochemical formulations improved agricultural productivity and increased the world food supply in recent years. However, repeated and even misuses of agrochemical formulations for long periods have led to the development of catastrophic impact globally on the ecosystems. Major ecological impacts commonly encountered include chemical resistance of pests and pathogens, chemical residues, environmental pollution, and endangered wildlifes. The substantial ecological deterioration is often accused to be the major causes of problems such as cancer, dysplasia and malfunction of the human immune system.

Despite the great disadvantages of agrochemical applications, the needs for agrochemical formulations continue growing steadily under the pressure of increasing population and soaring food demands. During the past decade, the annual consumption of agrochemical compositions globally estimates over 30 billion US dollars. The disadvantages of conventional agrochemical applications stimulate the development of biorational biopesticides, which has become a main stream of biotechnology undertaking worldwide. Microbial biocontrol agents are among these endeavors attracted greatest attention because of the wide application, the excellent control effect, and the best of all is the bountiful supportive resources from microbial biotechnology.

*Streptomyces* spp. are widespread gram-positive bacteria. More than 400 species have been described, most of them produce antibiotics. For disease control of plants, members of *Streptomyces* spp. have been used for over half a century. Streptomycin was the first to discover from *S. griseus* in 1943 and successfully applied it to prevent bacterial infestations on fruit trees and vegetables. With the success of streptomycin application, the use of antibiotic metabolites derived from *Streptomyces* spp. later became a predominant art for the control of certain foliar diseases on plants. From 1950 to 1970, quite a few *Streptomyces* derived antibiotics had been launched; notable examples included the use of Blasticidin-S and Kasugamycin for the control of rice blast disease (*Pyricularia oryzae* Cav.), and the use of Polyoxin and Validamycin for the control of sheath blight disease of rice (*Thanatephorus cucumeris* (Frank) Donk).

Since 1970, the control of soil-borne diseases began to draw increasing attention in regarding to the employment of *Streptomyces* spp. for plant protection. Successful examples included the application for the control of root rot on pea caused by *Rhizoctonia solani*, *Fusarium* wilt on cucurbits and carnations caused by *Fusarium oxysporum*, postharvest disease of various crops caused by *Aspergillus* spp., and some other important diseases caused by *Alternaria* spp., *Fusarium culmonum*, *Botrytis cinerea* and *Pythium ultimum*. The antibiotics applied among these cases are in essence biochemical property which appears to be inhibitory or lethal to the pathogens.

However, the safety of antibiotic application in agriculture has been challenged lately due to the increasing concern of the development of antibiotic resistance in medical treatment. The application of antibiotics for plant disease control is thus now facing unprecedented pressure due to the over exaggerated concern of the social public about the developing and transferring of the antibiotic resistance among pathogenic microbial populations.

In contrast to the concerns and difficulties in the development of antibiotics, the development of microbial biomass products have attracted great attention recently. The numbers of commercialized microbial biomass products are increasing; their efficacy of disease control is satisfactory. The commercialized products with worldwide recognition, to name a few, include the fungal products of *Gliocladium viride* and *Trichoderma* spp., and the bacterial biomass products of *Bacillus subtilis* and *Streptomyces griseus*. The use of beneficial microbial biomass products has been a routine application for long time as an additive feed for aquatic animals or domestic animals. The direct fed microbial products, generally quoted as "probiotics", used as additives in animal breeding are known having bioregulators function in an animal's body.

The efficacy of disease control by above mentioned microbial biomass products is featured by an interaction from multiple mechanisms including nutrient and space competition, antibiotic activity, improved nutrient availability and microbial diversity, improved plant growth and vigor, improved soil fertility and the enhanced disease resistance. It is worth to mention that the observed, antibiotic activity per se is contributed by the collective effect of cohorts of antibiotic derivatives rather than a single purified composition. The involvement of multiple mode of action offers great advantages that chemical resistance problems generally encountered in conventional chemical and biochemical pesticide application wouldn't likely to occur. What adds more value is that most of the microbial species used are beneficial for soil fertility and plant growth; their environmental-friendliness make them an ideal alternative tool for pest management especially where agricultural sustainability is taken into account.

For the success of development of a microbial biomass products, it is critical that (1) the isolated microorganisms must be generally regarded as safe (GRAS) for animals and humans; (2) the shelf life of the attempted product should be satisfactory when stored properly; (3) the field application should be convenient by common practices; and (4) the price, smell, and efficacy should be competitive for customer acceptance.

The development of *Streptomyces* spp. biocontrol formulation has been a hot topic for long time because the great potential for plant disease control. However, most of the existing art known so far has been devoted to explore the uses of antibiotics secreted. The only EPA registered *Streptomyces* spp. containing biomass product gaining wide recognition is Mycostop (Kemira Co. Ltd., Finland). Another product of this kind recently approved by EPA is Actinovate (Natural Industries Co. Ltd., USA). The product Mycostop is known to contain viable *S. griseovirides* mycelia and spores at the concentration of $10^8$ cfu/g; it was recommended for the control of soil-borne plant diseases. Actinovate is a *S. lyticus* biomass containing water dispersible granule, it is also recommended for the control of soil-borne diseases.

For preparation of a *Streptomyces* spp. viable inoculants in a large scale, conventionally it is done by solid fermentation in which wheat, oat or unpolished rice grains are the predominant growth substrates used. Because liquid fermentation is a widely used, rapid and easy method appropriate for preparing microbial inoculants in large volumes, a liquid product would be more preferable. However, the preparation of *Streptomyces* spp. biomass product by liquid fermentation in large scale is of great difficulty since the bacteria grow predominantly as mycelia balls rather than spores.

The present invention discloses a novel method that solves the problem of preparing high concentration viable *Streptomyces* spp. spore inoculant in large scale by liquid fermentation.

SUMMARY OF THE INVENTION

An aspect of the present invention relates to a biocontrol formulation comprising the following steps. A *Streptomyces* bacterium is selected simultaneously with superior sporulation ability, chitinase activity and antagonistic effectiveness against plant fungal pathogens by culturing with fungal pathogens, wherein the selected *Streptomyces* bacterium is cultured on a chitin-limited plate to assess the ability of sporulation and chitinase activity, and the *Streptomyces* bacterium with superior sporulation ability is the strain which producing abundant powder-like, mature, well dispersed spore chains. Spores from the selected bacteria are collected, and used as a seed inoculum. The seed inoculum is cultured to directly yield a broth medium containing well suspended spores at concentration greater than $5 \times 10^9$ spores/ml which can be diluted to provide a greater than $10^8$ spores/ml seed inoculum in the continued amplified production. The biocontrol formulation is obtained.

Preferably, the concentration of the source inoculum used to start out a new broth culture is at least $10^8$ viable spores/ml, and the concentration of the source inoculum is in a range of about $5.0 \times 10^9$ to $5.0 \times 10^{10}$ viable spores/ml.

Preferably, the broth medium is the Czapek's culture medium containing an organic nutrient source.

Preferably, the chitin-limited plate is a sugar-limited plate containing chitin as a major carbon source.

Preferably, the broth culture is amplified with the use of 10× series fermentors.

Preferably, the broth culture starts out from a 500 to 5000 ml shake-flasks with the seed inoculum prepared on a colloidal chitin amended potato sucrose agar (PSA) plate. The bacterial spores were washed off from the agar plate with sterilized distilled water, and adjusted to the desired concentration to serve as the seed inoculum.

Preferably, the followed stepwise seed inoculum amplification by using the broth culture produced at the previous steps which containing greater than $10^{10}$ viable spores/ml and well dispersed spore suspension.

Preferably, a condition for the followed stepwise amplifying cultures of the seed inoculum are at about 28 to 37° C., 80 to 250 rpm, 0.25 to 0.75 vvm and pH at 5.0 to 8.0. More preferably, for the stepwise culturing the seed inoculum the spores are cultured at 30° C. under continuous stirring at 200 rpm and aeration at 0.5 vvm for about 4 to 6 days.

An aspect of the present invention relates to a biocontrol formulation prepared according to the above method which comprises at least $10^{10}$ viable spores/ml and barely mycelial remains.

Preferably, the biocontrol formulation is stored at 6° C. for more than 10 months prior to use.

Preferably, the biocontrol formulation is a broth medium containing viable spores in a range of about $10^{10}$ spores/ml to $10^{11}$ spores/ml.

Further benefits and advantages of the present invention will become apparent after a careful reading of the detailed description.

DETAILED DESCRIPTION OF THE INVENTION

Figure 1:
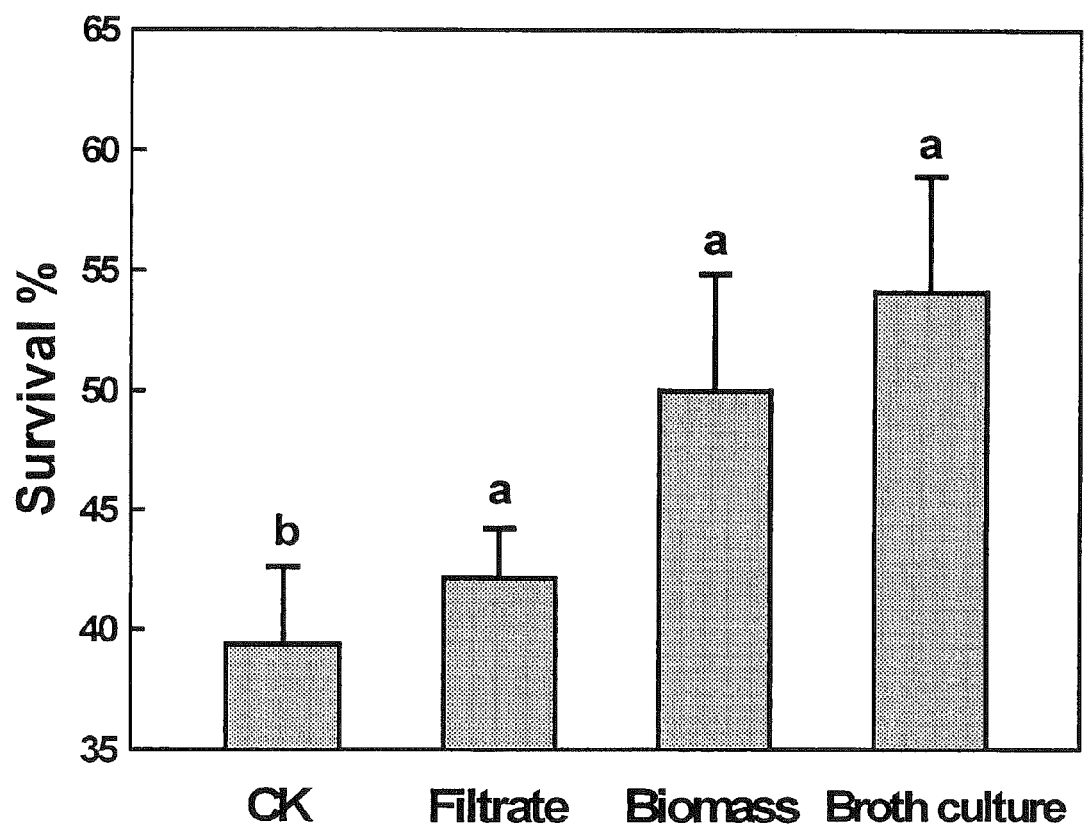
FIG. 1 is a bar chart showing the efficacy of cucumber plant disease control by application of a cultural filtrates, a biomass, a broth culture and a compared water treated control.

The present invention is about a biocontrol formulation containing *Streptomyces* spp., method for preparing the formulation and relevant use. The method according to the present invention includes selecting a *Streptomyces* strain with desired properties, culturing the selected strain and obtaining the formulation with a high density of spores. The criterion for selecting the desired properties of the *Streptomyces* strain includes selecting *Streptomyces* bacteria with superior sporulation ability, chitinase activity and antagonistic effectiveness against fungal pathogens by culturing with plant fungal pathogens.

To manufacture the present invention, a *Streptomyces* bacterium may be cultured on a chitin-limited medium or a PSA agar at about 30° C. for about 3 to 4 days, then the *Streptomyces* bacterium may be washed off by sterilized distill water to collect spores and form a spore suspension. The concentration of the spore suspension may be at least $10^8$ spores/ml, preferably, is about $2.0 \times 10^9$ to $5.0 \times 10^9$ viable spores/ml. The spore suspension may be further inoculated in a shake-flask for obtaining a small scale seed inoculum. The seed inoculum may be further amplified by a 10× series fermentors for continuous provision of a greater than $10^{10}$ viable spores/ml inocula as a source inoculum, and finally cultured in a traditional stirrer tank fermentor at the desired volume to obtain the agricultural biocontrol formulation with a high density of well-suspended spores.

The method described in the present invention could be operated in a traditional stirrer tank fermentor to obtain the desired formulation with at least $10^9$ viable spores/ml. Preferably, according to the method of present invention, the broth medium directly yields over $10^{11}$ cfu/ml of spore-enriched broth culture in a batch culture system, and the spores are well suspended and mycelial remains are hardly observed.

The present invention also relates to the formulation prepared by the above method. The formulation contains at least $10^9$ viable spores/ml, and the spores are well suspended. Suitable formulations will be known to those skilled in the art (wettable powders, granules and the like, or can be microencapsulated in a suitable medium and the like, liquids such as aqueous flowables and aqueous suspensions, and emulsifiable concentrates). Other suitable formulations will be known to those skilled in the art. The formulation also could be diluted for use.

According to the present invention, the selected *Streptomyces* strains obtained by the described method are shown to exhibit strong antagonism towards a wide range of fungal phytopathogens, including pathogens that cause pre- and post-emergence damping off of seedlings, root rot, brown rot and white rot. As such, the selected *Streptomyces* strains are particularly suitable as biocontrol agents that can be used to protect plants against infection by these phytopathogens. Thus, the selected *Streptomyces* strains are useful in methods for reducing the susceptibility of plants to fungal infection; plants treated with these microorganisms will show reduced effects of fungal infection.

The biocontrol formulation of the present invention is useful in a method of imparting to plants protection against plant pathogens. This method involves applying the biocontrol agent to plants, plant seeds, or soil surrounding plants under conditions effective to impart disease protection to the plants and to plants produced from the plant seeds.
definitions:

While the following terms are believed to be well understood by people with ordinary skill in the art, the following definitions are set forth to obviate any ambiguity in the explanation of the invention.

The term "formulation" is intended to mean a combination of active agent and another compound, carrier or composition, inert (for example, a detectable agent or label or liquid carrier) or active, such as an adjuvant.

The term "source inoculum" used as herein refers to a part of the broth culture containing greater than $10^9$ viable spores/ml, and source inoculum is prepared for stepwise amplification.

The term "seed inoculum" used as herein refers to an inoculum containing in a suitable medium for proliferation. A seed inoculum may be derived directly from a selected *Streptomyces* strain cultured on an agar plate or diluted from a source inoculum of a broth medium. For example, when a source inoculum containing greater than $10^9$ spores/ml is added into a suitable medium, the source inoculum is diluted by the medium and than taken as a seed inoculum.

The term "amplify" or "amplification" as used herein refers to make a selected *Streptomyces* strain proliferate or increase into a larger volume in a suitable medium.

The term "directly" used as herein refers to produce a broth medium containing at least $10^9$ viable spores/ml without mediate collection.

The term "well suspended" or "well suspension" used as herein refers to the obtained spores which are separated without the mycelial ball or without sticky polysaccharidal remains. The well-suspended spores may be in a form of short/limited spore chain.

The term "biopesticide" used herein refers to suppression of existing fungus populations in the soils or on plants to prevent fungus populations from becoming established in the soil or on the plants.

The term "superior sporulation ability" used herein refers to the ability of a *Streptomyces* strain that could produce mature spores. The mature spores produced by the selected *Streptomyces* strain are powder-like spore chains, that can be easily dispersed in water, and mycelial remains of the selected *Streptomyces* strain are barely when the spores produced approached their maturity on a nutrients-limited medium. The spore chains are predominantly linear and markably elongated (arthrospore type chains of 50-80 spores). The superior sporulation ability also means the ability that aerial mycelia of a selected *Streptomyces* strain upon their maturity to transform into spore chains.

The term "high" used herein refers to the concentration of spores is at least $10^8$ viable spores/ml.

The term "a small scale" used herein refers to the volume of the product is less than 5 L.

The term "a large scale" used herein refers to the volume of the product is more than 50 L.

The term "chitin-limited plate" used herein refers to a sugar-limited plate containing chitin as a major carbon source. A chitin-limited plate is also a nutrients-limited plate.

The term "biological control" or "biocontrol" used herein refers to control of a pathogen or insect by the use of a second organism.

The term "bacteria" includes any prokaryotic organism that does not have a distinct nucleus.

The term "culturing" refers to the propagation of organisms on or in medium of various kinds.

The term "antifungal" refers to a condition that the growth of fungi is inhibited or fungi are killed.

The term "whole broth culture" used herein refers to a liquid culture containing both cells and media. Cells may be spores, mycelia or mycelial remains.

The term "tested strain" used herein refers to a bacterial strain used for testing or understanding the mechanism caused by the strain. In the present invention, *Streptomyces* strains are used for testing. In a preferred embodiment, an isolated *Streptomyces* strain, such as an *S. saraceticus* SS31, or an *S. griseobrunneus* S3 (SGS3), is used as a test strain. The strain *S. saraceticus* SS31 was deposited to Agricultural Research Culture Collection (NRRL) having address—International Depositary Authority, 1815 N. University Street Peoria, Ill. 61604 U.S.A. on May 16, 2016. The strain *S. saraceticus* SS31 was granted accession number—NRRL B-67256. The strain *S. griseobrunneus* S3 (SGS3) was deposited to Agricultural Research Culture Collection (NRRL) having address—International Depositary Authority, 1815 N. University Street Peoria, Ill. 61604 U.S.A. on May 6, 2016. The strain *S. saraceticus* SS31 was granted accession number—NRRL B-67251.

EXAMPLES

This invention is illustrated further rather than limited by the following Examples. All of the references listed in the application are hereby incorporated by reference.

Example 1

Control of *Pythium* Damping Off Disease by Using *Streptomyces* spp.

With reference to FIG. 1, an isolated strain of *Streptomyces* spp., *S. griseobrunneus* S3, was used as a test strain to understand the relevant mechanism on plant disease control. The broth culture of *S. griseobrunneus* S3 obtained from the fermentor culture was filtered to separate solid biomass from the broth medium. The solid biomass was then resuspended with sterile distilled water to its original concentration. The whole broth culture, the culture filtrate and the water resuspended biomass were diluted 100 times with tap water each respectively and applied to cucumber seedlings artificially inoculated with *Pythium aphanidermatum*. The compared control plants were drenching treated with water (CK). The survival rates of the seedlings were then scored to show the disease control efficacy of each applied treatment. As shown in FIG. 1, the best efficacy of disease control was by the whole broth culture and next to that was by the biomass. The culture filtrate appeared to be the worst among them in regard to the disease control efficacy. The results demonstrated that the efficacy of disease control was due primarily to the effect of *Streptomyces* bacteria rather than antibiotics in the broth medium.

Example 2

Mechanism of Disease Control by *Streptomyces* spp.

Activities of antibiotics and hydrolytic enzymes are the major factors known responsible for the inhibition or killing of fungal pathogens by *Streptomyces* spp. Whereas for efficacy of disease control observed, it is generally believed to due to a collective effect of the multiple modes of action including space and nutrient competition, antibiosis, mycoparasitism, soil fertility improvement, plant growth promotion and disease resistance enhancement.

Figure 2:
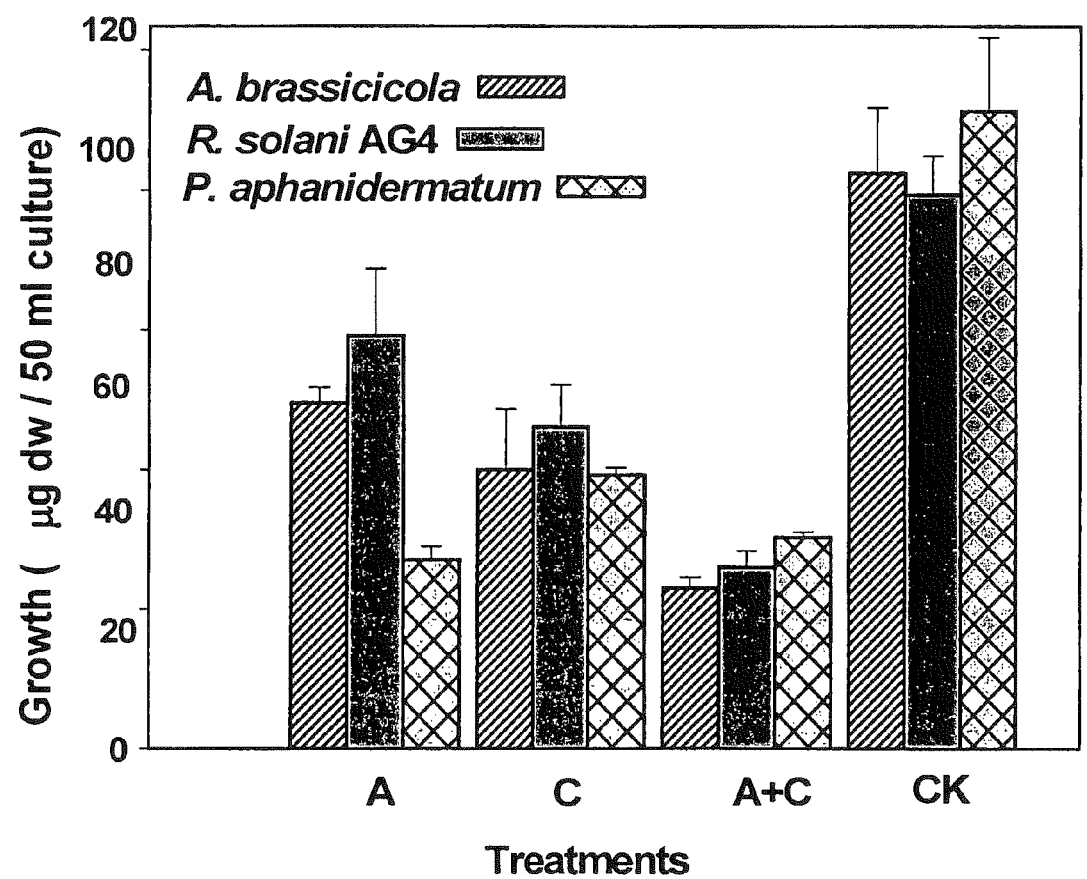
FIG. 2 is a bar chart showing the antifungal effect on tested fungi by an antibiotic and/or chitinase extracted from a *Streptomyces saraceticus* SS31 broth culture; the compared control was treated with water.

With reference to FIG. 2, an antibiotic (A) and a chitinase (C) were each respectively extracted from an *S. saraceticus* SS31 broth culture to illustrate their individual role in the anti-fungal activity of the test strain. The partially purified antibiotic and chitinase samples were tested in vitro respectively against *Alternaria brassicicola*, *Rhizoctonia solani* AG4 and *Pythium aphanidermatum*. The antibiotic (A) and chitinase (C) obtained from an SS31 strain cultured in a corn medium in accordance with the present invention were added to a potato sucrose broth medium each individually (A and C) or together (A+C) to test the effect on growth of *A. brassicicola*, *R. solani* AG4 and *P. aphanidermatum*. The control (CK) medium was treated with only water. The result of mycelial growth obtained showed that both the applied antibiotic and chitinase preparation are inhibitory to the growth of the three target fungi. The greatest inhibition shown in the A+C combined treatment further indicates the significance of synergistic effect in the antifungal activity of the tested *Streptomyces* strain.

Example 3

Effect of Nutrient on Growth and Antibiotic Activity of *Streptomyces* spp.

A liquid culture medium in accordance with the present invention was prepared to test the nutrient requirement of the tested strain. For an SS31 strain, the applicant had demonstrated that the use of polysaccharide as a carbon source favors greatly the secretion of antibiotic and chitinase.

For the tested Carbon sources shown in Table 1 and Table 2, it is clear that sucrose, chitin and starch are the best to promote secretion of antibiotic and chitinase. In the experiment performed, the tested carbon sources were added at the same concentration to replace sucrose for preparation of the Czapek's culture medium. The test bacteria were cultured at 30° C. under continuous shaking at 120 rpm. The control treatment was cultured in the same medium without sugar addition. Enzyme activity was tested by a dot blotting method, where that "−" means no enzyme activity; and "+, ++, +++, and ++++" each respectively indicate about equivalent to "10 to 20, 100, 200, and 400 units/ml" chitinase activity.

Table 2 shows results of antibiotic activity detected from these cultures wherein *Pythium aphanidermatum* was used as a target.

The results shown on Table 2 further indicated that antibiotics were secreted at the early phase of culturing, whereas chitinase was secreted at a later phase.

TABLE 1

Effect of Different Carbon sources on Chitinase Secretion by *S. saraceticus* SS31 Strain

| | Days after inoculation | | | | | |
|---|---|---|---|---|---|---|
| Treatment | 1 | 2 | 3 | 4 | 5 | 6 |
| Arabinose | − | − | − | +[1)] | + | − |
| Glucose | − | − | − | − | − | − |
| Mannitol | − | − | − | + | + | − |
| Sorbitol | − | + | + | ++ | ++ | + |
| Xylose | − | − | − | − | − | − |
| Lactose | − | − | − | − | − | − |
| Maltose | − | +− | + | + | − | − |
| Sucrose | + | + | ++ | +++ | +++ | ++ |
| Chitin | − | + | ++ | +++ | +++ | ++ |
| Starch | + | + | ++ | +++ | +++ | ++ |
| CK | − | − | − | − | − | − |

TABLE 2

Effect of Different Carbon sources on Antibiotic Secretion of *S. saraceticus* SS31 Strain Against *Pythium aphanidermatum*

| | Days after inoculation | | | | | |
|---|---|---|---|---|---|---|
| Treatment | 1 | 2 | 3 | 4 | 5 | 6 |
| Arabinose | $0.0_d$ | $1.3_{ef}$ | $1.0_f$ | $0.0_c$ | $0.0_d$ | $0.0_b$ |
| Glucose | $0.0_d$ | $0.0_g$ | $0.0_g$ | $0.0_c$ | $0.0_d$ | $0.0_b$ |
| Mannitol | $0.0_d$ | $0.0_g$ | $0.0_g$ | $0.0_c$ | $0.0_d$ | $0.0_b$ |
| Sorbitol | $0.0_d$ | $1.0_{fg}$ | $0.0_g$ | $0.0_c$ | $0.0_d$ | $0.0_b$ |
| Xylose | $1.0_c$ | $2.8_c$ | $1.5_{de}$ | $0.0_c$ | $0.0_d$ | $0.0_b$ |
| Lactose | $1.3_{bc}$ | $1.3_{ef}$ | $1.0_f$ | $0.0_c$ | $0.0_d$ | $0.0_b$ |
| Maltose | $0.0_d$ | $2.8_c$ | $1.8_{cd}$ | $1.0_c$ | $1.0_c$ | $0.0_b$ |

TABLE 2-continued

Effect of Different Carbon sources on Antibiotic Secretion of
S. saraceticus SS31 Strain Against Pythium aphanidermatum

| Treatment | Days after inoculation | | | | | |
|---|---|---|---|---|---|---|
| | 1 | 2 | 3 | 4 | 5 | 6 |
| Sucrose | $1.0_c$ | $8.3_b$ | $10.7_a$ | $7.2_a$ | $7.2_a$ | $3.0_a$ |
| Chitin | $0.0_d$ | $2.2_{cd}$ | $1.2_{ef}$ | $1.0_c$ | $1.0_c$ | $0.0_b$ |
| Starch | $11.1_a$ | $11.2_a$ | $8.3_b$ | $6.2_b$ | $6.2_b$ | $3.2_a$ |
| CK | $1.5_b$ | $1.5_{de}$ | $2.0_c$ | $0.0_d$ | $0.0_d$ | $0.0_b$ |

*The data shown was the width of inhibition zone formed by application of an SS31 strain culture filtrate against P. aphanidermatum, the larger the number, the greater the antibiotic activity. The numbers in each column followed by the same letters were not significantly different according to Duncan's new multiple range test (p = 0.05).

To ease the supply demand and as well to reduce the cost of main culture substrates needed for a large scale production, various cereal grains rich in starch contents were screened for the suitability as the main Carbon source in supporting the growth and chitinase secreting activity of the tested strains. The results shown in Table 3 indicated that with the presence of 1% of chitin, decoction of potato, corn and oat are among the tested natural grains the best to support the chitinase production.

Data shown in Table 3 are enzyme activity of the tested culture filtrate measured by a dot blotting assay as above described. The tested nutrient sources were added and tested same to that indicated in Table 1 except that 1% chitin was added in all tested treatments. The control treatment (CK) contained only 1% chitin as carbon source.

TABLE 3

Effect of various grain decoctions as supplements on chitinase
activity of S. saraceticus SS331 strain cultured in the Czapek's
medium where that 3% sucrose was replaced by 1% chitin

| Treatment | Days after inoculation | | | | | |
|---|---|---|---|---|---|---|
| | 1 | 2 | 3 | 4 | 5 | 6 |
| Oat | ++[1] | ++ | +++ | +++ | ++ | ++ |
| Adzuki bean | + | + | ++ | ++ | ++ | + |
| Soybean | + | + | + | + | + | + |
| Sorghum | + | + | ++ | ++ | + | + |
| Corn | +++ | +++ | +++ | +++ | +++ | +++ |
| Potato | +++ | +++ | +++ | +++ | +++ | +++ |
| CK(Chitin, 1%) | ++ | ++ | ++ | ++ | +++ | +++ |

Further, to the Czapek's medium wherein 3% sucrose was replaced by 0.15% chitin, the supplementation of pectin promoted significantly chitinase activity (Table 4). In contrast to this, the addition of cellulose and glucose appeared to be inhibitory. The method for the tested nutrients supplementation and the method for testing were the same as that described in Table 1, and the culture medium containing 0.15% chitin as the only carbon source was used as control (CK).

TABLE 4

Effect of different carbon sources as supplements on chitinase
activity of S. saraceticus SS331 strain cultured in the Czapek's
medium where that 3% sucrose was replaced by 0.15% chitin

| Treatment | Days after inoculation | | | | | |
|---|---|---|---|---|---|---|
| | 1 | 2 | 3 | 4 | 5 | 6 |
| Cellulose (0.15%) | ++[1] | + | ++ | +++ | +++ | +++ |
| Cellulose (0.75%) | − | + | + | ++ | ++ | ++ |

TABLE 4-continued

Effect of different carbon sources as supplements on chitinase
activity of S. saraceticus SS331 strain cultured in the Czapek's
medium where that 3% sucrose was replaced by 0.15% chitin

| Treatment | Days after inoculation | | | | | |
|---|---|---|---|---|---|---|
| | 1 | 2 | 3 | 4 | 5 | 6 |
| Glucose (0.12%) | − | ++ | ++ | ++ | ++ | ++ |
| Glucose (0.60%) | − | + | + | ++ | ++ | ++ |
| Pectin (0.12%) | +++ | +++ | +++ | +++ | +++ | +++ |
| Pectin (0.60%) | ++++ | ++++ | ++++ | ++++ | ++++ | ++++ |
| Starch (0.12%) | − | +++ | +++ | +++ | +++ | +++ |
| Starch (0.60%) | − | +++ | ++ | ++ | +++ | +++ |
| CK (chitin, 0.15%) | ++ | +++ | ++ | ++ | +++ | +++ |

Figure 3:
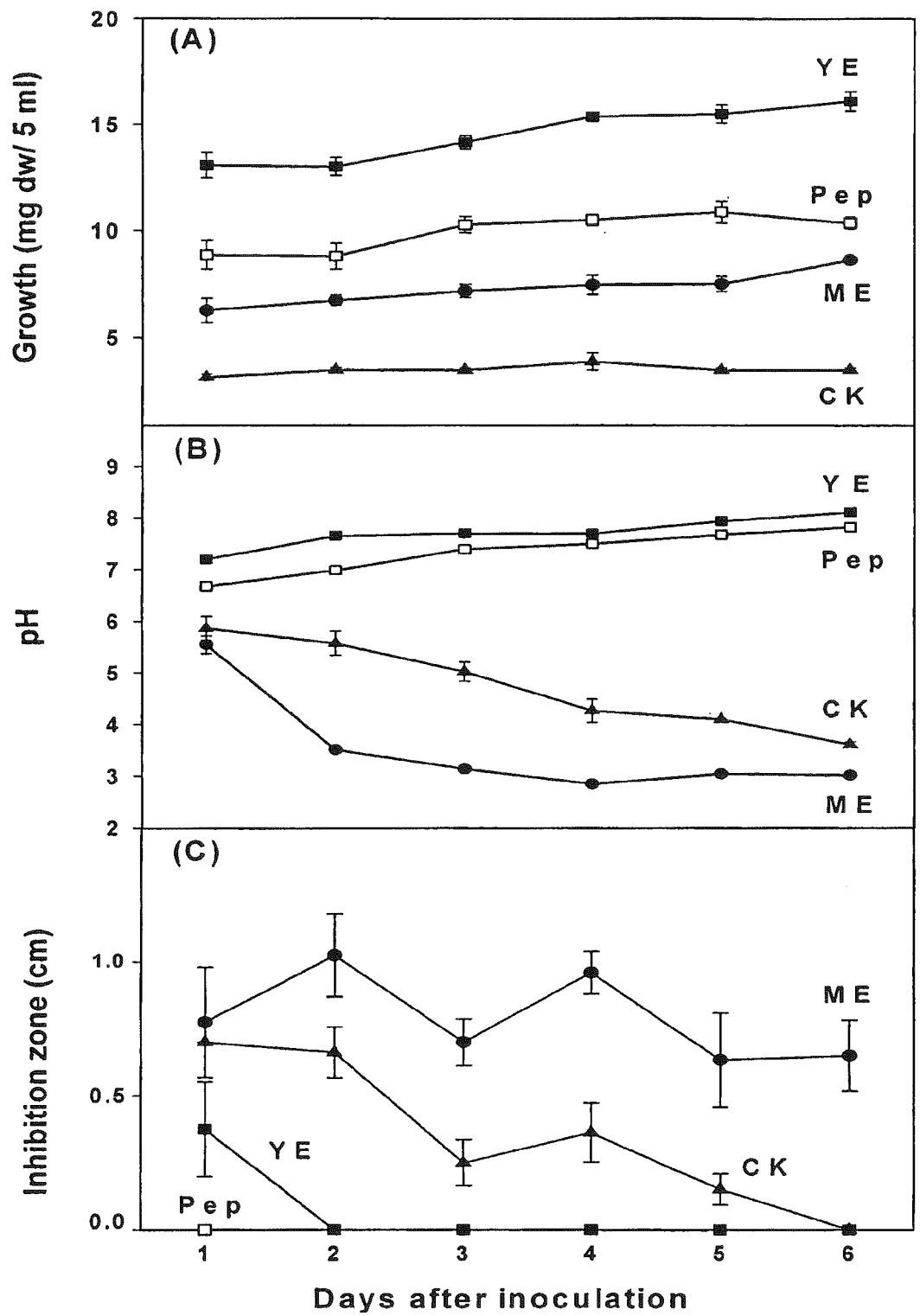
FIG. 3 is a chart showing the growth promoting effect of different growth factors on SS31.

As regards to requirement of growth factors, malt extract (ME), yeast extract (YE) and peptone (Pep) each at 1% (W/V), respectively, was tested for their effect as supplement on supporting the growth and chitinase activity of the Streptomyces spp. tester strains. By use of SS31 as the tester strain, the dry weight and antibiotic activity of the culture were determined by a time course. As that shown in FIG. 3, the addition of ME, YE and Pep, especially YE promoted greatly the growth of the tested strain. It was also noted during the course of study that addition of ME showed great promoting effect on both the sporulation and the antibiotic activity. And in accompany to that was the rapid decrease of pH of the growth medium to around 3.0 to 4.0. In contrast to this, the growth promoting effect of YE and Pep was accompanied with a reducing antibiotic activity (especially Pep) and the slight increase of the medium pH.

Figure 4:
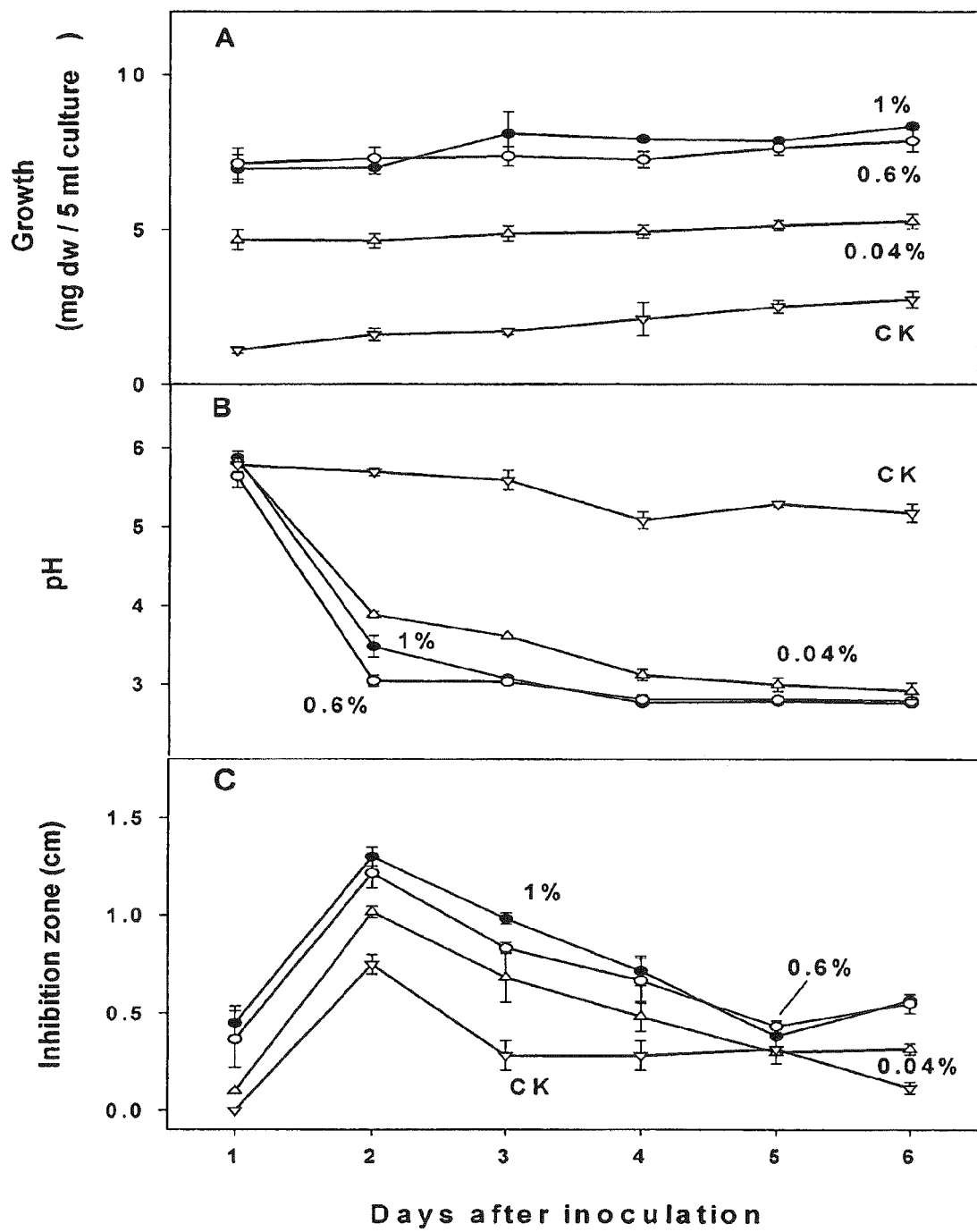
FIG. 4 is a chart showing the stimulating effect of malt extract at different concentrations on chitinase secretion of SS31.

In another trial, the effect of these growth factors on chitinase activity expression was tested. The addition of the test growth medium by 1% ME, Pep and yeast powder all showed stimulating effect on the chitinase activity of the tester strain SS31 (Table 5). The stimulating effect appeared to be most prominent in ME supplementation (Table 5). The stimulating effect of ME, however, was slightly reduced when yeast powder was added additionally to the culture (YP+ME). In conclusion, malt extract appeared to be among the test growth factors the best for growth promotion, antibiotic activity, and as well chitinase activity expression of the tester bacteria. The inventors further tested different concentrations of malt extract to understand the effect on growth of bacteria and antibiotic activity. The results are shown in FIG. 4. Significant growth promotion was detected with the amendment of malt extract at as low as 0.04%. The addition of malt extract at 0.6% showed a significantly increased growth promotion that was nearly equivalent to that by 1.0% malt extract addition.

TABLE 5

Effect of growth factor supplementation on the chitinase activity
expression of S. saraceticus SS31 strain growing in the Czapek's
medium. The tested growth factors malt extract (ME), yeast powder
(YP) and peptone (Pep) were each respectively added to basic medium,
and chitinase activity of the culture filtrate was determined
by dot blotting assay as above described.

| Treatment | Days after inoculation | | | | | |
|---|---|---|---|---|---|---|
| | 1 | 2 | 3 | 4 | 5 | 6 |
| ME | − | ++[1] | ++ | ++ | ++ | ++ |
| Pep | − | + | + | ++ | ++ | ++ |
| YP | − | + | + | ++ | ++ | ++ |

TABLE 5-continued

Effect of growth factor supplementation on the chitinase activity expression of *S. saraceticus* SS31 strain growing in the Czapek's medium. The tested growth factors malt extract (ME), yeast powder (YP) and peptone (Pep) were each respectively added to basic medium, and chitinase activity of the culture filtrate was determined by dot blotting assay as above described.

| Treatment | Days after inoculation | | | | | |
|---|---|---|---|---|---|---|
| | 1 | 2 | 3 | 4 | 5 | 6 |
| YP + ME | − | + | + | ++ | ++ | ++ |
| CK | − | − | − | − | ++ | ++ |

Example 4

A Chitinase Activity, Antibiotic Activity and Sporulation Competence (CAS) Collective Screening Method for Selecting Appropriate *Streptomyces* spp. Strains Antagonistic effectiveness, survival nature and competitiveness among microorganisms in the residing environment are the major determinative factors for the potential of a microbial strain to be a successful biocontrol agent. The importance of survival nature indicated spores as a preferred entity for the employment of a *Streptomyces* spp. strain for biopesticide application. It was thus then sporulation becomes a critical feature to be considered in addition to the antibiotic activity and hydrolytic enzyme activity.

A CAS screening method in accordance with the present invention was used to assess chitinase activity (C), antibiotic activity (A) and sporulation competence (S) of *Streptomyces* strain tested. For assessment of antibiotic activity, the tester strain was dual cultured on a PSA plate consisting of potato decoction (P), sucrose (S) and agar (A) with pathogens including *Pythium aphanidermatum* (member of Oomycetes), *Alternaria brassicicola*, *Pyricularia oryzae* and *Rhizoctonia solani* AG4 (the later three are members of Fungi Imperfecti with Teliomorph associated with Ascomycetes or Basidiomycetes). 50 μl spore suspension of different tester *Streptomyces* strains were put on the filter paper (0.50 cm diameter) at the edge of Petri plate, and at the center were the mycelial discs of the targeted fungal pathogen *P. oryzae*. The dual cultures were incubated in the dark at 28° C. for 2 to 5 days, and colonies developed were scored for the amount of sporulation and the width of inhibition zone.

Further, with the use of glycochitin amended in the Czapek's agar medium wherein sugar and nitrogen supply were substantially reduced, the sporulation and chitinase activity of the tested strain were screened. For assessment of sporulation ability, a *Streptomyces* strain with powder-like spores or with visible spore chains was selected. The development of the clear zone due to chitinase degradation and the amount of sporulation were scored. For assessment of chitinase activity, a *Streptomyces* strain produced a large clear zone was selected.

By application of this CAS collective screening method, approximately 20 of *Streptomyces* spp. strains with superior antibiotic and chitinase activity and excellent sporulation characteristics were selectively identified from 219 chitinolytic rhizosphere *Streptomyces* strains isolated. The potential of the selected strains for biopesticide developments have been well illustrated by the performance of the model strains as above mentioned.

Example 5

Establishment of Technique Platform for Liquid Fermentation in a Large Scale The mass production was aimed to produce by pilot scale traditional stirrer tank fermentor a *Streptomyces* broth culture with high density of viable spores. For the establishment of the technique platform, *Streptomyces saraceticus* SS31 strain was used as a model isolate. The model isolate was selectively screened by the above described the CAS method repeatedly to keep its competence of antibiosis and sporulation throughout the test. With the use of 5 L to 750 L serial conventional stirrer tank liquid fermentor, the tester strain was shown to yield an over $10^{11}$ cfu/ml of spore-enriched broth culture in a batch culture system. Furthermore, the spore biomass produced appeared to be stable when stored at cold. The survival count of the liquid sample stored at 6° C. for 8 months remained exceeding $5 \times 10^8$ cfu/ml.

5.1 Inoculum Preparation

The model isolate was smeared on a chitin amended potato sucrose agar plate (containing potato decoction 200 g/l, sugar 20 g/l, agar 15 g/l and colloidal chitin 20 g/l) and incubated in the dark at 30° C. for about 4 to 6 days. The spores generated were collected and suspended with sterile distilled water. To serve as the "primary inoculum" for the fermentation trials, the spore concentration was quantitated and adjusted to $A_{620}=0.5$ by a spectrophotometer which is equivalent to approximately $10^{10}$ cfu/ml of the tester strain.

The primary inoculum can be then amplified to a larger scale by either a solid or a liquid culture system. The solid culture generally uses oat or wheat grains as culture substrate. For liquid culture, the medium used consisted mainly 1.5 to 3.5% (w/v) finely-milled oat milk, 0.3 to 0.5% (w/v) molasses and malt extract. And depend on the amount of inoculum preparation needed, the liquid culture may be performed by an Erlenmeyer flask or a small size fermentor system. The primary inoculum was applied to the freshly prepared liquid medium to $1 \times 10^8$ cfu/ml of final concentration, and the culture was incubated at 30° C. under continuous stirring at 200 rpm and aeration at 0.5 vvm. The sporulation generally achieved its high plateau after culturing for 4 to 6 days. The spore enriched biomass thus obtained was then used as "seed inoculum" for the large scale production.

5.2 Preparation of Culture Media

The culture medium for large scale fermentation contains mainly a basic medium with amendment of 1 to 3% (w/v) oat, wheat or corn as organic nutrients. The basic medium may be a modified the Czapek's culture broth or a half/full strength the Hoagland's nutrient solution. The modified Czapek's culture broth consists of $K_2HPO_4$ 0.7 g/L, $KH_2PO_4$ 0.5 g/L, $MgSO_4 \cdot 7H_2O$ 0.5 g/L, $FeSO_4 \cdot 7H_2O$ 0.01 g/L and $ZnSO_4$ 0.001 g/L.

The fresh grains used were well-soaked in water and were milled into fine powder with a diameter less than 50 μm. The growth factors were added to the culture medium, and 20 g optional colloidal chitin and molasses were added. The culture medium was adjusted to about pH 7.0 before autoclaved.

5.3 Parameters of Large Scale Fermentation

The fermentation was carried out by batch culture in a traditional stirring type liquid fermentor. The "seed inoculum" of the tester strain was added to the autoclaved culture medium to approximately $10^8$ cfu/ml in final concentration. The culture was kept at 30° C., 80 to 250 rpm and an aeration at 0.25 to 0.75 vvm. The pH of the culture medium was maintained at about 5.0 to 8.0 range. The culture was sampled daily to monitor the status of growth throughout the cultural period.

5.4 Results of Mass Production

Figure 5:
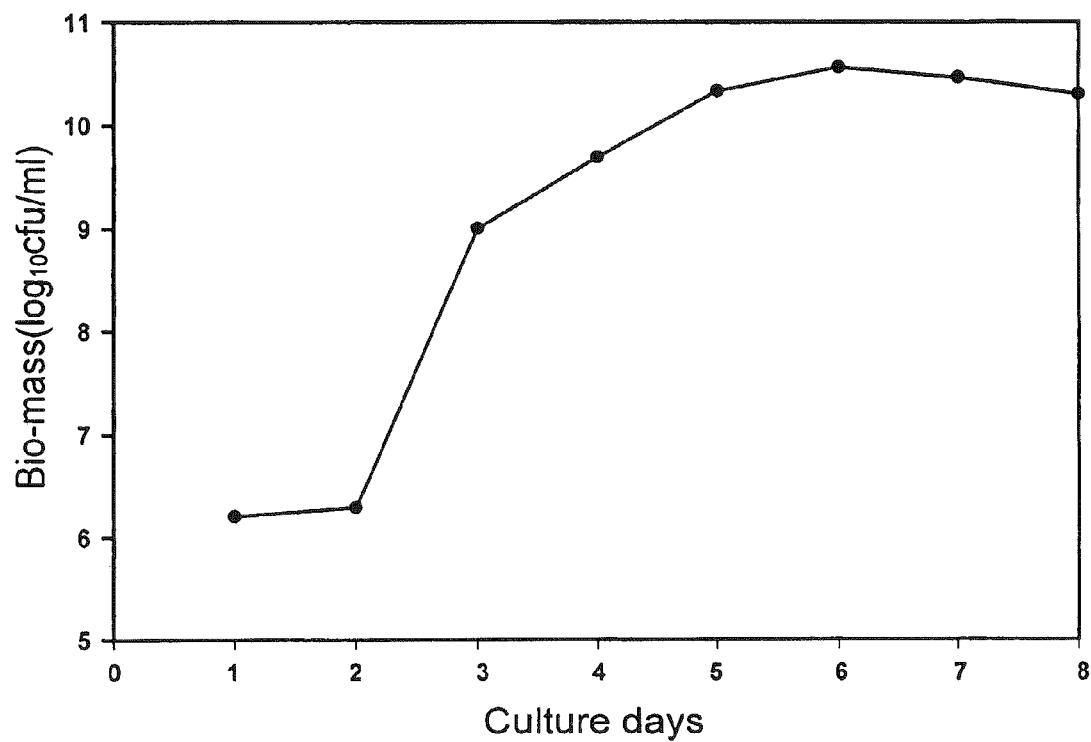
FIG. 5 is a graph showing the yield of an SS31 strain cultured in a 5 liters fermentor by use of oat containing liquid medium in accordance with the present invention.
Figure 6:
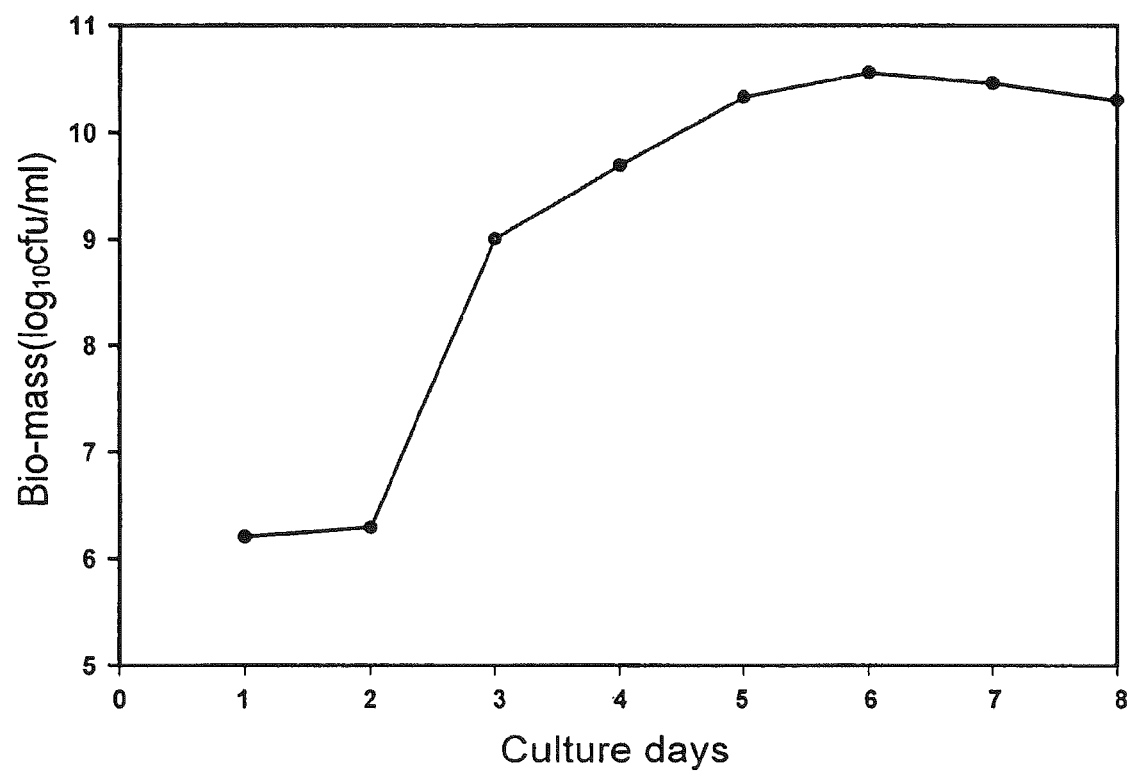
FIG. 6 is a graph showing the yield of an SS31 strain cultured in a 750 liters fermentor by use of a oat containing liquid medium in accordance with the present invention.
Figure 7:
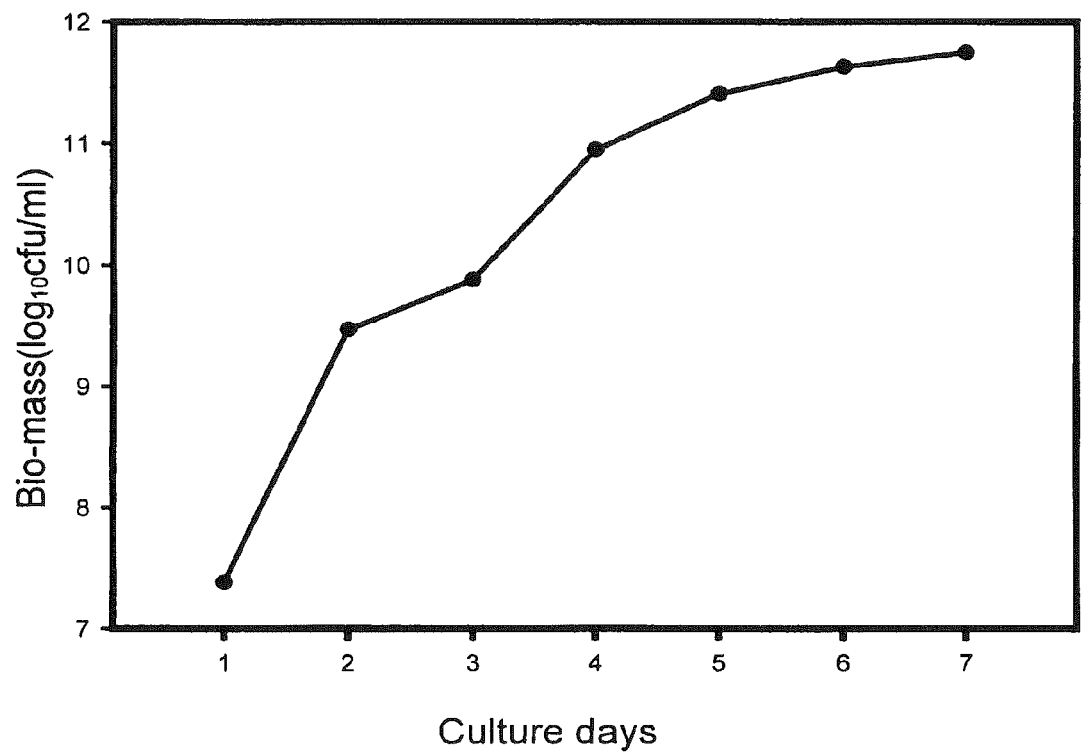
FIG. 7 is a graph showing the yield of an S3 strain cultured in a 750 liters fermentor by use of a oat containing liquid medium in accordance with the present invention.

The trial production was performed with the use of 5 L to 750 L pilot scale fermentor wherein finely grinded oat milk and pectin were applied as major carbon sources. With reference to FIG. 5, the yield of tester strain SS31 in a 5 L fermentor reached $10^{10}$ cfu/ml four to five days after inoculation. Furthermore, the high yield of spore biomass was repeatable when the scale of production was upgraded to a 50 to 750 L level fermentor. With reference to FIGS. 6 and 7, the yield of spore biomass of both SS31 and S3 terster strains, in the same growth medium, all exceeded $10^{11}$ cfu/ml 5 to 6 days after inoculation.

5.5 Stability of the Large Scale Fermentation Product

The biomass products of tester *Streptomyces* prepared by the above described method had an earthy fragrance typical of Actinomycetes. The broth culture appeared to be light to dark grayish in color, somewhat sticky. The bacteria biomass tended to settle into two phases without agitation; whereas it became well suspended readily when stirred. It is clear that the sample consists mainly numerous spores of the tested strain, and the mycelial remains were hardly observed. The spores were mostly oval-shape, the size of S3 spores is about twice of that of SS31.

The stability of storage is a critical factor for the practical application of the attempted microbial products. The broth cultures obtained from the liquid fermentor in a serial trial production was stored in a walk-in cold room at 6° C. And the survival of the spore propagules was examined by a monthly schedule by dilution plate method. With reference to Tables. 6 and 7, most of the tested samples remained at a level over $10^8$ cfu/ml after being stored for 8 to 10 months. The stability of the microbial preparation appeared to be satisfactory.

TABLE 6

Stability of SS31 strain culture broth from a batch of trial production when stored at 6° C.

| | Formulation | | | |
| --- | --- | --- | --- | --- |
| | Sample 1 | Sample 2 | Sample 3 | Sample 4 |
| | | CFU | | |
| Storage time | OP0919 | O1003 | OP1003 | CP1003 |
| 0 month | $4.4 \times 10^{10}$ | $4.0 \times 10^{10}$ | $3.6 \times 10^{10}$ | $8.4 \times 10^{9}$ |
| 1 month | $1.5 \times 10^{10}$ | $2.2 \times 10^{9}$ | $2.9 \times 10^{10}$ | $3.0 \times 10^{9}$ |
| 2 months | $5.9 \times 10^{9}$ | $8.6 \times 10^{8}$ | $1.3 \times 10^{9}$ | $2.9 \times 10^{8}$ |
| 3 months | $6.3 \times 10^{8}$ | $9.1 \times 10^{8}$ | $8.6 \times 10^{8}$ | $2.3 \times 10^{8}$ |
| 4 months | $7.0 \times 10^{8}$ | $4.5 \times 10^{8}$ | $4.4 \times 10^{8}$ | $3.0 \times 10^{8}$ |
| 5 months | $6.5 \times 10^{8}$ | $4.0 \times 10^{8}$ | $4.0 \times 10^{8}$ | $2.0 \times 10^{8}$ |
| 8 months | $4.1 \times 10^{8}$ | $5.0 \times 10^{8}$ | $4.5 \times 10^{8}$ | $1.3 \times 10^{8}$ |

*The data presented are the survival rate of the spores (CFU/ml) after indicated storage time.

TABLE 7

Stability of SS31 strain culture broth from another batch of trial production when stored at 6° C.

| | Formulation | | |
| --- | --- | --- | --- |
| | Sample 1 | Sample 2 | Sample 3 |
| | | CFU | |
| Storage time | 100/200 | 150 | 200 |
| 0 month | $1.6 \times 10^{10}$ | $8.4 \times 10^{9}$ | $5.3 \times 10^{9}$ |
| 1 month | $4.3 \times 10^{9}$ | $1.5 \times 10^{9}$ | $3.5 \times 10^{9}$ |
| 2 months | $5.5 \times 10^{9}$ | $3.9 \times 10^{9}$ | $5.7 \times 10^{9}$ |
| 3 months | $4.7 \times 10^{9}$ | $1.5 \times 10^{9}$ | $1.8 \times 10^{9}$ |
| 4 months | — | — | — |
| 5 months | — | — | — |
| 6 months | $4.0 \times 10^{9}$ | $1.2 \times 10^{9}$ | $1.7 \times 10^{9}$ |
| 7 months | $9.1 \times 10^{8}$ | $7.0 \times 10^{8}$ | $1.1 \times 10^{9}$ |
| 8 months | $8.7 \times 10^{8}$ | $7.2 \times 10^{8}$ | $9.3 \times 10^{8}$ |
| 9 months | $7.9 \times 10^{8}$ | $7.5 \times 10^{8}$ | $9.0 \times 10^{8}$ |
| 10 months | $6.0 \times 10^{8}$ | $4.0 \times 10^{8}$ | $6.0 \times 10^{8}$ |

*The data presented are the survival rate of the spores (CFU/ml) after indicated storage time.

Example 6

Efficacy of Disease Control by Application of the Broth Culture of Tester Strains 6.1 Application of *Streptomyces* spp. Products for the Control of Damping Off Diseases The *Streptomyces* spp. products were applied by spraying or drenching on the tested plants artificially inoculated with the target fungal pathogen. The results obtained demonstrated the efficacy of the attempted *Streptomyces* spp. as useful products for controlling diseases caused by *P. aphanidermatum* and *R. solani* AG4.

Figure 8:
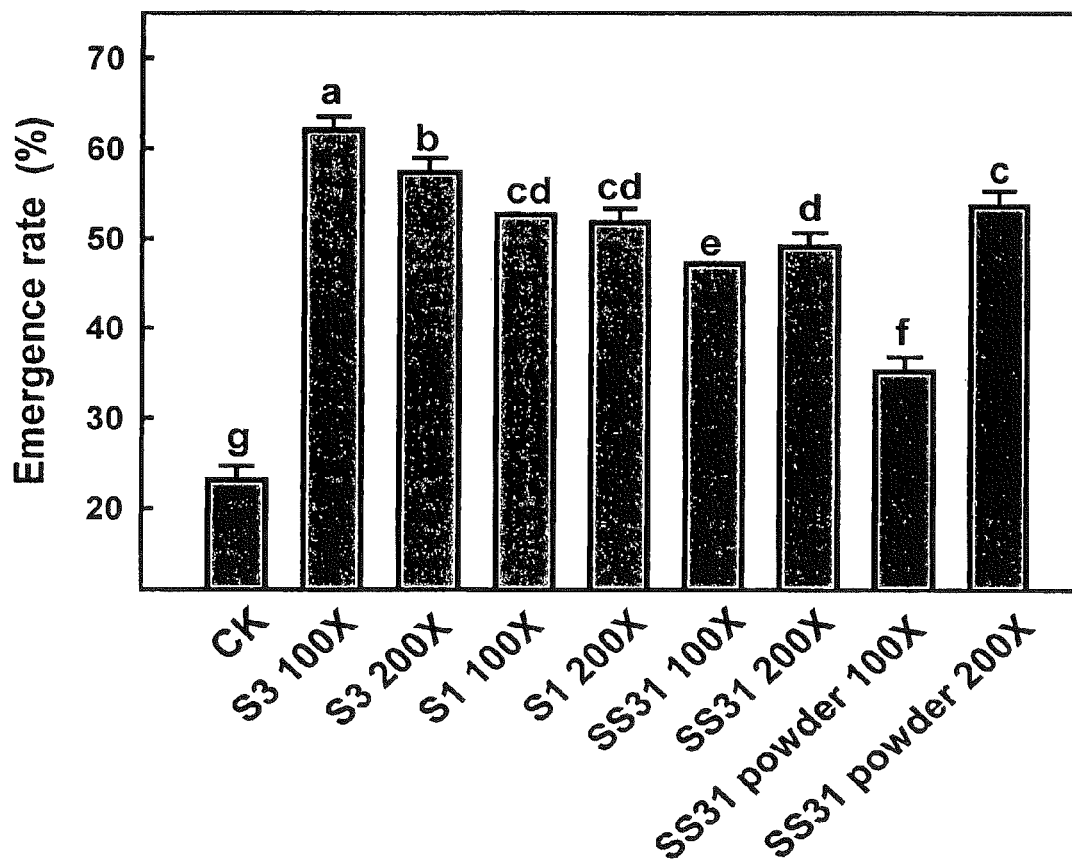
FIG. 8 is a graph showing the efficacy of cucumber damping off disease control by application of S1, S3 and SS31 strains in comparison to that of water treated control.

6.1.1 Control of Cucumber Damping Off Disease Caused by *P aphanidermatum* in Greenhouse The tested formulations included culture broths of S1, S3, and SS31 strains and a powder formulation of SS31 strain. The test samples each at 100 to 200× dilutions were drenching applied, at 1 ml per plant, onto the cucumber seedlings growing on a soil-mix artificially inoculated with *P. aphanidermatum*. The control plants (CK) were drenched with only water. With reference to FIG. 8, the emergence rate indicated clearly the effectiveness of disease control by the tester *Streptomyces*.

6.1.2 Control of Seedling Blight of Sweet Pepper Caused by *R. solani* AG4 in Greenhouse The broth culture of tester strains S3 and SS31 were each drenching applied at 50 to 100× in dilution onto the sweet pepper plants artificially inoculated with *R. solani* AG4. The results of emergence rate and average severity index (ASI) of tested plants shown in Table 8 demonstrated the great capability of the tester strains in the control of the targeted disease.

TABLE 8

Control of seedling blight of greenhouse grown sweet pepper caused by *R. solani* AG4.

| Treatment [a] | Emergence rate (%) [b] | ASI [c] |
| --- | --- | --- |
| CK | 19.4 ± 2.2 | 4.3 ± 0.1 |
| SS31 100X | 33.3 ± 2.2 | 3.7 ± 0.1 |

TABLE 8-continued

Control of seedling blight of greenhouse grown
sweet pepper caused by R. solani AG4.

| Treatment [a] | Emergence rate (%) [b] | ASI [c] |
|---|---|---|
| S3100X | 37.5 ± 1.6 | 3.4 ± 0.1 |
| S3 50X | 55.6 ± 2.2 | 2.3 ± 0.1 |

[a] The tested seedlings were each drenching treated with the tester strain twice; the first time at seeding with 0.6 ml/plant, and the second time at two weeks later with 1 ml/plant.
[b] Percentage of plants emerged and successfully established.
[c] Disease severity was rated by a 5-class scale. (1 = healthy plant; 2 = primary root and ground part remained firm but became necrotic; 3 = primary root tip turn soft and rotting, and root-hair hardly left; 4 = death and rotting of seedlings emerged; 5 = seeds not emerged and dead).

6.1.3 Effectiveness of Soil Treatment in Reducing Inoculum Potential of R. solani AG4

The spores of tester strain SS31 collected from culture on oat grain were formulated into powder ($10^{10}$ cfu/g of spore) with the use of corn starch as carrier. A peat moss growth medium was autoclaved and evenly mixed with mycelial propagules of R. solani AG4 to serve as infested soil for the performed test. The pathogen infested soil was then treated with SS31 spore suspension, and the corn starch amended powder formulation each respectively. The infested soil sample without the amendment treatment and that treated with only corn starch were used as compared control (CK). The tested samples were collected weekly and the survival of the target pathogen was determined by a selective method where that seeds of Bahia grass (Paspalum notatum Flugge) were used as a selective tool. The results shown on Table 9 indicated clearly that the density of R. solani AG4 in the test sample receiving the powder formulation (SS31/corn) declined very fast, and followed to that was the sample treated with SS31 alone. As a contrast, the propagule density of R. solani AG4 in the two control treatment showed only slight decline or no significant changes. The quick decline of the pathogen propagule density was clearly a function of the SS31 tester strain amended; whereas the best effectiveness of the powder formulation implicated the enhancement of corn starch on the antibiotic activity of applied bacteria.

TABLE 9

| DAT* | CK | Corn starch | SS31 | SS31 + corn starch |
|---|---|---|---|---|
| 1 week | 100 | 100 | 98 | 82 |
| 2 weeks | 95 | 98 | 87 | 30 |
| 3 weeks | 93 | 96 | 65 | 5 |
| 4 weeks | 90 | 93 | 49 | 4 |

*DAT: days after treatment. Data presented were average of percentage of Bahia grass seeds shown positive colonization of the target pathogen.

Figure 9:
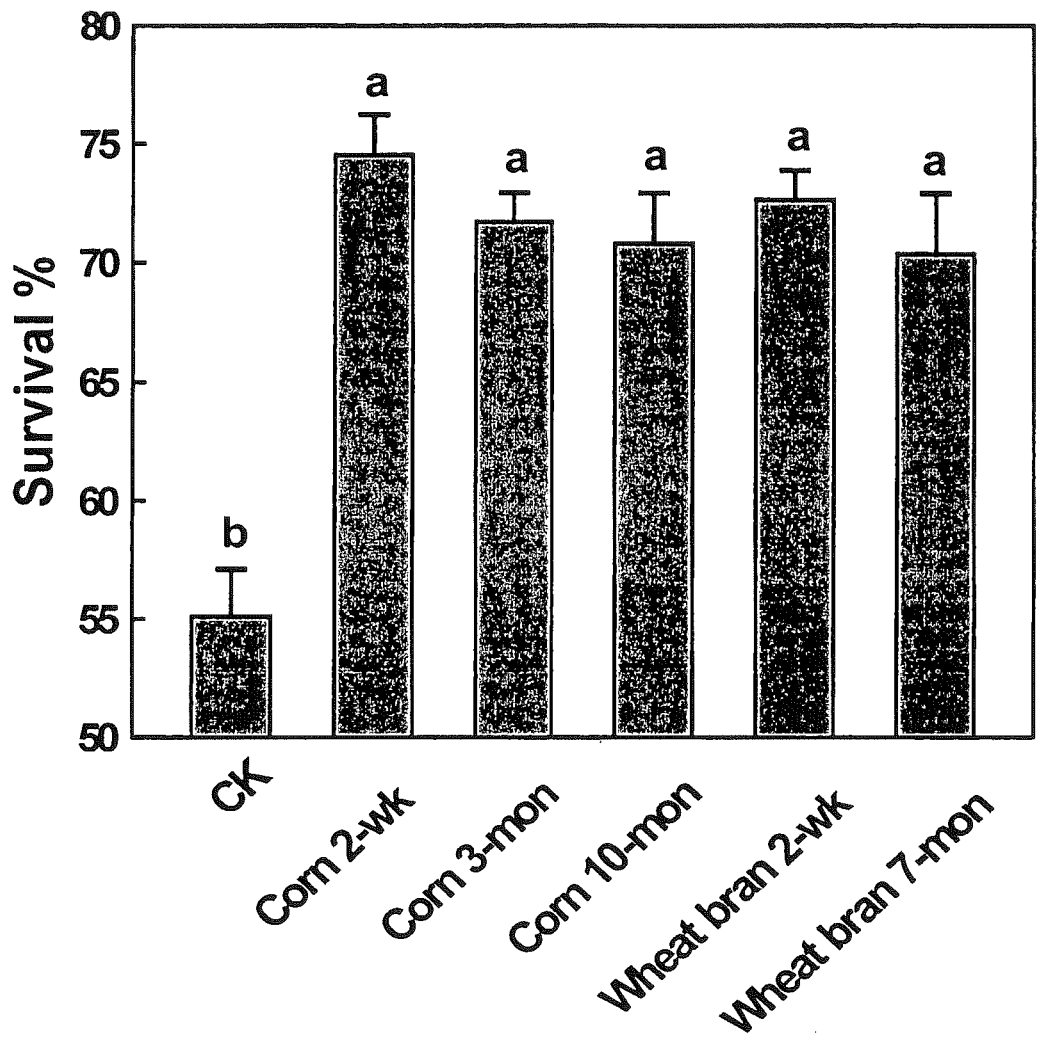
FIG. 9 is a graph showing the efficacy of cucumber damping off disease control by application of different formulation of S3 strain after stored at 6° C. for 3 to 10 months.

6.1.4 Effect of Long Term Storage on Efficacy of Disease Control by the Broth Culture of the Tester Strain The broth culture of tester strain S3 produced from wheat bran- and corn starch-based broth medium were stored in a cold room at 6° C. for 7-10 months. The samples with different terms of storage shown on FIG. 9 were screened for their efficacy of damping off disease control using cucumber seedlings as tested system. The tested greenhouse grown plants which were artificially inoculated with P. aphanidermatum were drenching treated with a 400× diluted broth culture. The efficacy of disease control scored 2 weeks after treatment indicated that all the tested sample formulations provided nearly equally-well the protection against the pathogen infection. The disease control efficacy of both corn and wheat bran cultural broths after 3-10 months storage was nearly the same as that by the ones stored only for 2 weeks.

In another trial the fresh prepared broth culture of SS31 tester strain grown in a growth factor fortified oat broth medium (new formulation-O) was compared to that after one year storage at 6° C. (new formulation-O/1 year). Drenching treatment of cucumber seedlings artificially inoculated with P. aphanidermatum were drenching treated with the tested broth cultures each at 100× in dilution. Also included in the test was a broth culture grown in corn broth medium with growth factor fortified (new formulation-C) and a broth culture grown in oat broth medium without growth factor fortified (Old formulation-O). The compared control plants (CK) were drench treated with only water. The results obtained indicated that the fresh prepared new formulation/O was among the applied treatments the best for the disease control, the severity index of the treated plants was 18%. As a comparison, the severity index of the fresh prepared Old formulation-O was 35%, whereas that of New formulation-O/1 year was 40%. The performance of New formulation/C was among them the worst as regard to the effectiveness of disease control.

6.1.5 Control of Fruit Infection of Papaya by Phytophthora palmivora in the Field The field grown papaya (Carica papaya cv. Tainung No. 2) trees with severe fruit infection by P. palmivora were spray-treated by the broth culture of tester strain SS31 grown in oat broth medium at 500× in dilution by a weekly schedule for 6 consecutive times. Papaya plants sprayed by phosphorus acid (1000 ppm) with pH adjusted to 6.5 by KOH were used as a comparison by chemical treatment. The field trial was performed for two consecutive years in the same field plot. The control plants were sprayed with water. The disease incidence was surveyed 1 week after the last spray treatment. For the water treated control plants, the rate of fruit infections were 23% and 37% for the $1^{st}$ and the $2^{nd}$ year trial respectively. As a comparison, disease incidence on plants treated with the tester Streptomyces broth culture were 7% and 3% respectively, whereas that by chemical fungicide treatment were 8% and 9% respectively.

6.1.6 Control of Citrus Foot Rot/Huanglungbing Like Disease Complex by Tested Streptomyces Strain Citrus plants over 10 years old in Taiwan are often suffered from serious problem of growth deterioration. Infected citrus trees mostly displayed symptoms of complex infection of foot rot disease and Huanglungbing-like infection. Although a mycoplasma infection has been known to be the likely cause of Huanglungbing, the characteristics of symptom development indicate clearly the effect of soil deterioration and root malfunctioning wherein the role of certain cryptic soil borne pathogen may take into account. To explore the possible use of tester Streptomyces formulation for the control of soil borne disease, citrus trees with prominent foot rot infection and Huanglungbing like disease symptoms in the field were drenching treated with the trial products on a regular basis. Results obtained showed that the application of the tester Streptomyces products stopped the foot rot infection and improved significantly the growth vigor. And best of all, the new leaves developed appeared to be relieved from the Huanglungbing like infections.

6.1.6.1 Control of Foot Rot Infection on Young Seedlings

Six field grown one year old sweet orange seedlings with characteristic foot rot infection symptoms including yellowing and even defoliation starting from the lower leaves were selected, and drenching treated with a 200× diluted tester Streptomyces product once per month for two consecutive times. Disease survey was performed one month after the second application. Four of the treated plants showed revived growth, although the other two test seedlings died.

The potential of the attempted product in the disease control application was clearly indicated.

6.1.6.2 Disease Control Among the Fully Developed Citrus Plants

A 25 year old orange orchard severely plagued by the foot rot/Huanglungbing disease complex was used for the trial. A total of 21 plants were used. Among them, 8 were drenching treated with tester strain SGS3, 7 were treated with tester strain SS31, and the other 6 plants were drenched with water to serve as the control treatment. As that shown on Table 11, the experiment was conducted starting from Apr. 10, 2002. All the test plants were treated for 3 consecutive times on the dates shown; each test plant were drenched with approximately 60-80 liters of the 100× diluted broth cultures. The disease severity index of each plant was scored before each drenching treatment and about one month after the last treatment. The results shown on Table 11 indicated clearly the efficacy of the tester strains in relieving the disease complex symptoms as compared to that of water treated control plants.

TABLE 11

| Treatment | Nos. of plants tested | April 10 | May 24 | June 18 | July 29 |
|---|---|---|---|---|---|
| Control | 6 | 2.5 ± 0.2a | 2.5 ± 0.2a | 1.2 ± 0.2a | 1.2 ± 0.2a |
| Tester strain SGS3 | 8 | 2.8 ± 0.2a | 1.9 ± 0.1b | 0.4 ± 0.2b | 0.1 ± 0.1b |
| Tester strain SS31 | 7 | 2.7 ± 0.2a | 2.0 ± 0.2ab | 0.4 ± 0.2b | 0.6 ± 0.2b |

Data in Table 11 is average disease index, and the number followed by different letters indicates the significant difference according to Duncan's multiple range test (p=0.05).

Although the invention has been explained in relation to its preferred embodiment, many other possible modifications and variations can be made without departing from the spirit and scope of the invention as hereinafter claimed.

What is claimed is:

1. A method for large scale preparation of a biocontrol formulation comprising a high concentration of viable Streptomyces spp. spores, the method comprising:
   culturing a Streptomyces bacterium selected from the group consisting of *Streptomyces saraceticus* SS31 and *Streptomyces griseobrunneus* S3 on a sugar-limited plate containing chitin as a major carbon source, wherein the Streptomyces bacterium has antagonistic efficacy against plant fungal pathogens and sporulation competence;
   collecting spores from the Streptomyces bacterium;
   culturing the spores to obtain a seed inoculum; and
   amplifying the seed inoculum in broth medium in a large-scale serial fermentor at about 28 to 37° C., 80 to 250 rpm, 0.25 to 0.75 vvm and pH at 5.0 to 8.0 to directly yield a biocontrol formulation comprising the broth medium containing at least $10^9$ viablespores/ml,
   wherein the broth medium is modified Czapek's culture medium containing 1% (w/v) to 3% (w/v) oat, wheat, or corn,
   optionally 0.12-0.6% (w/v) pectin,
   0.15% (w/v) or 1% (w/v) chitin, and 0 to 1.0% (w/v) malt extract.

2. The method as claimed in claim 1, wherein the seed inoculum obtained is at a concentration of at least $10^8$ viable spores/ml.

3. The method as claimed in claim 1, wherein collecting spores from the Streptomyces bacterium comprises
   washing off the Streptomyces bacterium by sterilized distilled water from a colloidal chitin added potato sucrose agar (PSA) plate to form a spore suspension.

4. The method as claimed in claim 1, wherein the seed inoculum is obtained by liquid culturing in a shake-flask.

5. The method as claimed in claim 4, wherein the shake-flask is a 500 to 5000 ml shake-flask.

6. The method as claimed in claim 1, wherein amplifying the seed inoculum comprises stepwisely amplifying the seed inoculum with the use of 10X series fermentors.

7. The method as claimed in claim 1, wherein the conditions for amplifying the seed inoculum are at 30° C. under continuous stirring at 200 rpm and aeration at 0.5 vvm for about 4 to 6 days.

8. The method as claimed in claim 1, wherein the sugar-limited plate containing chitin as a major carbon source is a potato sucrose agar (PSA) plate consisting of potato decoction, sucrose, agar and colloidal chitin.

9. The method as claimed in claim 1, wherein the biocontrol formulation comprises viable spores at a concentration of about $10^{10}$ spores/ml to $10^{11}$ spores/ml.

* * * * *